United States Patent [19]

Krumme et al.

[11] 4,336,458

[45] Jun. 22, 1982

[54] DIAGNOSTIC RADIOLOGY APPARATUS FOR PRODUCING LAYER IMAGES OF AN EXAMINATION SUBJECT

[75] Inventors: Hans J. Krumme, Uttenreuth; Martin Schmidt, Erlangen; Guenter Schmitt, Erlangen; Wolfgang Schubert, Erlangen, all of Fed. Rep. of Germany

[73] Assignee: Siemens Aktiengesellschaft, Berlin & Munich, Fed. Rep. of Germany

[21] Appl. No.: 191,430

[22] Filed: Sep. 29, 1980

[30] Foreign Application Priority Data

Oct. 24, 1979 [DE] Fed. Rep. of Germany ....... 2943027

[51] Int. Cl.[3] .......................... A61B 6/00; G01T 1/20; H01J 35/16

[52] U.S. Cl. ................................ 250/445 T; 250/367; 250/508

[58] Field of Search ............ 250/416 TV, 445 T, 367, 250/505, 508, 385

[56] References Cited

U.S. PATENT DOCUMENTS 4,292,525 9/1981 Tschunt ......................... 250/445 T 4,292,538 9/1981 Carlson .......................... 250/445 T

*Primary Examiner*—Alfred E. Smith

*Assistant Examiner*—T. N. Grigsby

*Attorney, Agent, or Firm*—Hill, Van Santen, Steadman, Chiara & Simpson

[57] ABSTRACT

In an exemplary embodiment, a measuring arrangement for irradiating the examination subject from different directions has a radiation source, a radiation receiver, and a computer connected to the radiation receiver for computing the attenuation values of specific image points of the irradiated body layer from the output signals of the radiation receiver. A collimator is present with a collimator grid compartment for each detector of the radiation receiver. Every detector is comprised of a scintillator crystal and a photoelectric transducer. The scintillator crystal is mounted on the surface of the photoelectric transducer such that the transducer is disposed between the associated collimator plate and the scintillator crystal. The scintillator crystal is coated, on its surface, with the exception of the surface confronting the photoelectric transducer, with an optical seal which can be light-reflecting on its side resting against the scintillator crystal.

4 Claims, 3 Drawing Figures

DIAGNOSTIC RADIOLOGY APPARATUS FOR PRODUCING LAYER IMAGES OF AN EXAMINATION SUBJECT

BACKGROUND OF THE INVENTION

The invention relates to a diagnostic radiology apparatus for producing layer images of an examination subject, comprising a patient support, comprising a measuring arrangement for irradiating the examination subject from various directions having a radiation source which emits a radiation beam penetrating the layer to be examined whose extent perpendicular to the layer plane is equal to the layer thickness, and a radiation receiver which supplies electric output signals corresponding to the measured radiation intensity, and comprising a computer, connected to the radiation receiver, for computing, from the output signals of the radiation receiver, the attenuation values of specific image points of the irradiated body layer, wherein the radiation receiver has a row of detectors and a collimator is present with one collimator grid compartment for each detector, and wherein every detector is arranged in its collimator grid compartment on a metal plate of radiation-absorbing material which bounds the grid compartment and every detector is compressed of a scintillator crystal and a photoelectric transducer optically in contact therewith, which transducer is mounted on the metal plate.

A diagnostic radiology apparatus of this type, a so-called computer-tomograph, is described in the German patent application P 28 40 965.6 and in the corresponding U.S. application for patent Ser. No. 068,230 filed Aug. 20, 1979. In this diagnostic radiology apparatus, an optimum protection of the detectors of the radiation receiver against stray radiation is provided, because the detectors are disposed in the collimator grid compartments and are thus protected from stray radiation by the collimator plates. An individual detector can here be readily exchanged by removing the plate on which it is mounted from the collimator and replacing it with another plate with a different detector.

SUMMARY OF THE INVENTION

The object underlying the present invention resides in further developing a diagnostic radiology apparatus of the type initially cited such that an improved light efficiency (or yield) of the scintillation light takes place.

In accordance with the invention this object is achieved in that the scintillator crystal is mounted on the surface of the photoelectric transducer such that the transducer is disposed between the plate and the scintillation crystal and in that the scintillator crystal is coated with an optical seal on its surface, with the exception of the surface lying against the photoelectric transducer. In the case of the diagnostic radiology apparatus it is possible to obtain a large-area (or surface) contact between the photoelectric transducers and the scintillator crystals of the detectors and hence to obtain a good light efficiency (or yield). The light efficiency (or yield) is even further improved if the optical seal is light-reflecting on its side lying against the scintillator crystal.

In the following, the invention shall be explained in greater detail on the basis of two exemplary embodiments illustrated in the accompanying drawing sheet; and other objects, features and advantages will be apparent from this detailed disclosure and from the appended claims.

DETAILED DESCRIPTION

Figure 1:
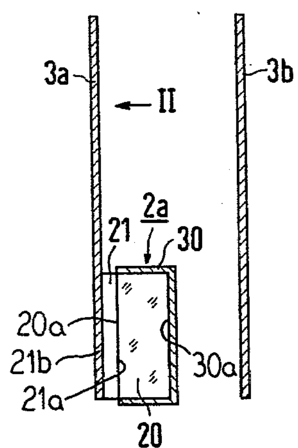
FIGS. 1 and 2 illustrate two views of the parts of a diagnostic radiology apparatus in accordance with the invention which are significant in terms of the invention.

In FIG. 1 two metal plates 3*a* and 3*b* of a collimator corresponding to FIG. 4 of the referenced prior U.S. patent application are illustrated. The plates 3*a*, 3*b*, consisting of X-ray absorbing material; e.g. tantalum, here bound a collimator grid compartment in which a detector 2*a* is arranged. The detector 2*a* consists of a scintillator crystal 20; e.g. a cesium iodide/thallium crystal (a CsI/T1-crystal) and a photoelectric transducer 21; e.g. a photodiode. The photoelectric transducer 21 is securely cemented on the plate 3*a*. On the side 21*a* of the transducer 21 disposed opposite the cemented side 21*b* the scintillator crystal 20 is securely cemented, so that the photoelectric transducer 21 lies between the plate 3*a* and the scintillator crystal 20. The scintillator crystal 20 is coated with an optical seal 30 on its surface, with the exception of the surface 20*a* which confronts the surface 21*a* of the photoelectric transducer 21, which optical seal 30 is light reflecting on its side 30*a* lying against the scintillator crystal 20. The optical seal can, for example, be a vapor-deposited aluminum layer or a light-reflective lacquer. The light efficiency (or yield) is very high due to the large-area (or surface) contact (at 20*a*, 21*a*) between the photoelectric transducer 21 and the scintillator crystal 20, and because of the reflective optical seal 30 at the remaining five surfaces of the scintillator crystal 20.

Figure 2:
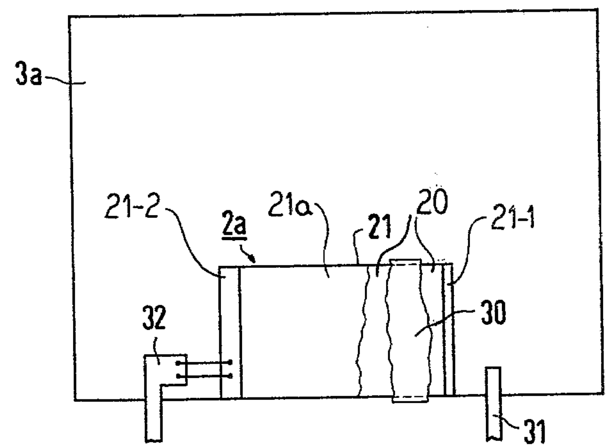

From FIG. 2, which shows the plate 3*a* in a view in direction of the arrow II in FIG. 1, it is apparent that the plate 3*a* is provided with a cathode feed line 31 which makes electrical contact with the cathode of the photodiode via the metal of plate 3*a*. The one pole 21-1 of the photoelectric transducer 21 is thus conveyed-off via the plate 3*a*. The other pole 21-2 is in electrical contact with an anode connection 32 applied in an insulated fashion on the plate 3*a*.

Figure 3:
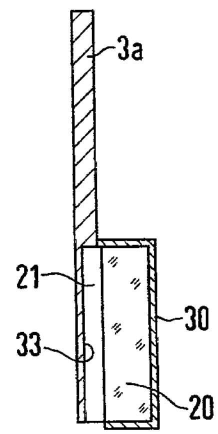
FIG. 3 illustrates a variant of the exemplary embodiment according to FIGS. 1 and 2.

In the variant illustrated in FIG. 3, the collimator plate 3*a* exhibits a recess 33 in which the photoelectric transducer 21 is disposed. It can there be connected with the plate 3*a*, for example, by means of an electrically conductive epoxy resin adhesive bond. The scintillator crystal 20 can be connected with the photoelectric transducer 21 by means of a transparent epoxy resin adhesive bond.

The disclosure of U.S. Ser. No. 068,230 filed Aug. 20, 1979 is incorporated herein by reference to show other details of construction of an exemplary embodiment, by way of background.

It will be apparent that many modifications and variations may be effected without departing from the scope of the novel concepts and teachings of the present invention.

We claim as our invention:

1. Diagnostic radiology apparatus for producing layer images of an examination subject, comprising a patient support, a measuring arrangement for irradiating the examination subject from different directions having a radiation source which emits a radiation beam penetrating the layer to be examined whose extent perpendicular to the layer plane is equal to the layer thickness, and having a radiation receiver which supplies electric output signals corresponding to the measured radiation intensity, and a computer connected to the radiation receiver for computing the attenuation values of specific image points of the irradiated body layer from the output signals of the radiation receiver, the radiation receiver having a row of detectors having a collimator with one collimator grid compartment for each detector and having a plate supporting every detector in the collimator grid compartment associated with and providing radiation-absorbing material bounding the grid compartment and having a scintillator crystal and a photoelectric transducer optically in connection therewith, said photoelectric transducer being mounted on the plate, characterized in that the scintillator crystal (20) is mounted on the surface of the photoelectric transducer (21) such that the transducer is disposed between the plate (3*a*) and the scintillator crystal (20), the scintillator crystal (20) being coated with an optical seal (30) on its surface, with the exception of the surface confronting the photoelectric transducer (21).

2. Diagnostic radiology apparatus according to claim 1, characterized in that the optical seal (30) is light-reflecting on its side adjacent the scintillator crystal (20).

3. Diagnostic radiology apparatus according to claim 1, characterized in that the plate (3*a*) has a recess (33) therein, and the photoelectric transducer (21) is disposed in said recess (33) of the associated plate (3*a*).

4. Diagnostic radiology apparatus according to claim 2, characterized in that the plate (3*a*) has a recess (33) therein, and the photoelectric transducer (21) is disposed in said recess (33) of the associated plate (3*a*).

* * * * *